United States Patent [19]

Bauer et al.

[11] Patent Number: 4,496,543

[45] Date of Patent: Jan. 29, 1985

[54] POLYPEPTIDES, PROCESSES FOR THEIR PRODUCTION, PHARMACEUTICAL COMPOSITIONS COMPRISING SAID POLYPEPTIDES AND THEIR USE

[75] Inventors: Wilfried Bauer, Lampenberg; Janos Pless, Basel, both of Switzerland

[73] Assignee: Sandoz Ltd., Basel, Switzerland

[21] Appl. No.: 524,374

[22] Filed: Aug. 18, 1983

[30] Foreign Application Priority Data

Aug. 24, 1982 [CH] Switzerland ........................ 5031/82

[51] Int. Cl.$^3$ ...................... A61K 37/00; C07C 103/52
[52] U.S. Cl. ................................ 514/11; 260/112.5 S; 514/16
[58] Field of Search .................. 260/112.5 S; 424/177

[56] References Cited

U.S. PATENT DOCUMENTS

| | | | |
|---|---|---|---|
| 4,235,886 | 11/1980 | Freidinger et al. | 260/112.5 S |
| 4,282,143 | 8/1981 | Sarantakis | 260/112.5 S |
| 4,360,516 | 11/1982 | Freidinger et al. | 260/112.5 S |
| 4,395,403 | 7/1983 | Bauer et al. | 260/112.5 S |

Primary Examiner—Delbert R. Phillips

Attorney, Agent, or Firm—Gerald D. Sharkin; Robert S. Honor; Thomas O. McGovern

[57] ABSTRACT

Straight-chain or mono-cyclicpolypeptides comprising a heptapeptide moiety, said moiety having in the 1-position (N-terminal) an α-N-phenylalkylated, optionally ring-substituted phenylalanine residue, in the 2-position a cysteine residue, in the 3-position an optionally ring-substituted phenylalanine residue, in the 4-position an optionally benzene-ring-substituted tryptophan residue, in the 5-position an optionally ε-N-alkylated lysine residue and in the 7-position (C-terminal) a cysteine or cysteinol residue the S-atoms of the cysteine residue at the 2-position and the cysteine or cysteinol residue at the 7-position being linked together in the case of the mono-cyclic polypeptides to form an -S-S-bridge, whereby the residues at the 1-, 2-, 4-, 6-, and 7-positions of said heptapeptide moiety may each be in the (L)- or (D)-configuration and the residues at the 4-, 5- and 6-positions of said heptapeptide moiety may each be optionally α-N-alkylated, said polypeptides being in free or protected form, as well as salt forms and complexes thereof. Subject compounds are useful as pharmaceuticals, e.g. as GH-secretion inhibitors.

17 Claims, No Drawings

POLYPEPTIDES, PROCESSES FOR THEIR PRODUCTION, PHARMACEUTICAL COMPOSITIONS COMPRISING SAID POLYPEPTIDES AND THEIR USE

The present invention provides novel polypeptides, processes for their production, pharmaceutical compositions comprising said polypeptides and their use as pharmaceutically active agents.

More particularly the present invention provides a straight-chain or mono-cyclic polypeptide comprising a heptapeptide moiety, said moiety having in the 1-position (N-terminal) an α-N-phenylalkylated, optionally ring-substituted phenylalanine residue, in the 2-position a cysteine residue, in the 3-position an optionally ring-substituted phenylalanine residue, in the 4-position an optionally benzene-ring-substituted tryptophan residue, in the 5-position an optionally ε-N-alkylated lysine residue and in the 7-position (C-terminal) a cysteine or cysteinol residue the S-atoms of the cysteine residue at the 2-position and the cysteine or cysteinol residue at the 7-position being linked together in the case of the mono-cyclic polypeptides to form an —S—S-bridge, whereby the residues at the 1-, 2-, 4-, 6-, and 7-positions of said heptapeptide moiety may each be in the (L)- or (D)-configuration and the residues at the 4-, 5- and 6-positions of said heptapeptide moiety may each be optionally α-N-alkylated, said polypeptide being in free or protected form; as well as salts and complexes thereof. Preferred polypeptides in accordance with the invention are those of formula I

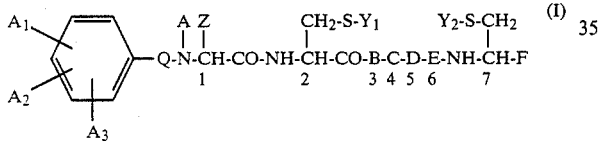

wherein

A is hydrogen, $C_{1-3}$alkyl or the acyl residue of an organic or inorganic acid, $A_1$ is hydrogen, $C_{1-3}$alkyl, $C_{1-3}$alkoxy, halogen, OH, $NO_2$, an esterified or amidated carboxy group or an amide group, $A_2$ is hydrogen, $C_{1-3}$alkyl, $C_{1-3}$alkoxy, halogen, OH or $NO_2$, $A_3$ is hydrogen, $C_{1-3}$alkyl, $C_{1-3}$alkoxy or halogen, Q is $C_{1-4}$alkylene, >N—CH(Z)—CO— is an (L)- or (D)-phenylalanine residue optionally ring-substituted by one or more members selected from the group consisting of halogen, $NO_2$, $NH_2$, OH, $C_{1-3}$alkyl and $C_{1-3}$alkoxy, B is —Phe— optionally ring-substituted by one or more members selected from the group consisting of halogen, $NO_2$, $NH_2$, OH, $C_{1-3}$alkyl and $C_{1-3}$alkoxy, C is —Trp— or —(D)Trp— optionally α-N-methylated and optionally benzene-ring-substituted by one or more members selected from the group consisting of halogen, $NO_2$, $NH_2$, OH, $C_{1-3}$alkyl and $C_{1-3}$alkoxy, D is —Lys— optionally α-N-methylated and optionally ε-N-$C_{1-3}$alkylated, E is the residue of a natural α-amino acid or of a corresponding (D)-amino acid, said residue being optionally α-N-methylated, F is a group of formula —$COOR_1$, —$CH_2OR_2$,

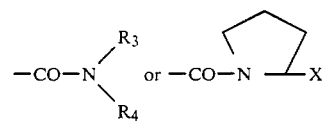

wherein $R_1$ is hydrogen or $C_{1-3}$alkyl, $R_2$ is hydrogen or the residue of a physiologically acceptable, physiologically hydrolysable ester, $R_3$ is hydrogen, $C_{1-3}$alkyl, phenyl or $C_{7-10}$phenylalkyl, $R_4$ is hydrogen, $C_{1-3}$alkyl or, when $R_3$ is hydrogen or methyl, also a group of formula —CH($R_5$)—X, $R_5$ is hydrogen, —$(CH_2)_2$—OH or —$(CH_2)_3$—OH, or represents the substituent attaching to the α-carbon atom of a natural α-amino acid and X is a group of formula —$COOR_1$, —$CH_2OR_2$ or —$CON(R_6)R_7$ wherein $R_1$ and $R_2$ have the meanings given above, $R_6$ is hydrogen or $C_{1-3}$alkyl and $R_7$ is hydrogen, $C_{1-3}$alkyl, phenyl or $C_{7-10}$phenylalkyl, the group —CH($R_5$)—X having the (D)- or (L)-configuration and $Y_1$ and $Y_2$ are each hydrogen or together represent a direct bond, whereby the residues in the 2- and 7-position each independently have the (L)- or (D)-configuration, and with the proviso that (L)- and/or (D)-cysteine residues are present at the 2- and 7-positions only, said polypeptide of formula I being in free or protected form; as well as salts and complexes thereof.

Throughout the present specification and claims by "halogen" is meant fluorine, chlorine and bromine. In accordance with conventional practice, amino acid residues referred to by abbreviation, e.g. —Phe—, —Cys— etc., are to be understood as having the (L)-configuration unless otherwise indicated.

Acyl residues as A include, in particular, the acyl residues of organic carboxylic acids (including e.g. amino acids and carboxyl terminated di- and oligopeptides), sulfonic acids, sulfaminic acids and carbonic acids and their derivatives. Suitable acyl residues are, e.g. the groups:

1. $R^I$CO— wherein $R^I$ is an aliphatic, cycloaliphatic, aromatic or heterocyclic group, especially $C_{1-20}$alkyl, $C_{3-20}$alkenyl, $C_{3-20}$alkinyl, phenyl, naphthyl or $C_{7-10}$(phenylalkyl);
2. $R^{II}SO_2$— wherein $R^{II}$ is $C_{1-10}$alkyl, phenyl or $C_{7-10}$(phenylalkyl);
3. $R^{III}O$—CO— wherein $R^{III}$ is $C_{1-10}$alkyl or $C_{7-10}$(phenylalkyl); and

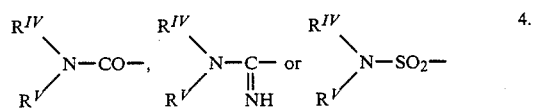

wherein $R^{IV}$ is hydrogen, $C_{1-10}$alkyl, phenyl or $C_{7-10}$(phenylalkyl) and $R^V$ is hydrogen or $C_{1-10}$alkyl.

Aliphatic groups as $R^I$ may be saturated or unsaturated, branched- or straight-chain. Similarly alkyl, alkenyl and alkinyl groups as well as the alkyl-moieties of phenylalkyl groups recited as $R^I$ through $R^V$ may all be branched- or straight-chain. All groups recited as $R^I$ through $R^V$ may optionally bear further substituents. Suitably groups recited as $R^I$ through $R^V$ are unsubstituted.

The phenyl ring of the phenylalkyl group at the α-N atom of the residue at the 1-position of the heptapeptide moiety of the polypeptides of the invention may be substituted, e.g. as in the case of polypeptides of formula I, wherein one or more of $A_1$, $A_2$ and $A_3$ is/are other than hydrogen, or unsubstituted. Furthermore the alkylene moiety of such phenylalkyl groups, e.g. groups Q in formula I, may be branched or straight-chain.

In the polypeptides of formula I, the following significances or combinations thereof are preferred.

5. A is hydrogen, $C_{1-3}$alkyl or a group $R^ICO-$ or $R^{II}SO_2-$ as defined under 1. and 2. above. More preferably A is hydrogen, $C_{1-3}$alkyl or $R^ICO-$, especially hydrogen or $R^ICO-$.
5.1 When A is a group $R^ICO-$, $R^I$ is preferably $C_{1-15}$alkyl, phenyl or $C_{7-10}$(phenylalkyl), more especially $C_{1-15}$alkyl, in particular $C_{1-10}$alkyl, e.g. $CH_3(CH_2)_8-$.
5.2 When A is a group $R^{II}SO_2-$, $R^{II}$ is preferably $C_{1-10}$alkyl or phenyl optionally substituted by $C_{1-3}$alkyl, especially phenyl or mono- or di-$C_{1-3}$alkyl-substituted phenyl. Most preferably $R^{II}$ is $C_{1-10}$alkyl.
6. $A_1$ is hydrogen; an esterified or amidated carboxy group of formula $R_8O-CO-$ or $R_8-NH-CO-$ respectively, wherein $R_8$ is $C_{1-16}$alkyl, or an amide group of formula $R_9-CO-NH-$ wherein $R_9$ is $C_{1-15}$alkyl. More preferably $A_1$ is hydrogen or a group $R_8-NH-CO-$, wherein $R_8$ is $C_{1-16}$alkyl, especially $C_{1-10}$alkyl, e.g. $CH_3(CH_2)_9-$. Most preferably $A_1$ is hydrogen.
7. $A_2$ is hydrogen.
8. $A_3$ is hydrogen.
9. Q is methylene.
10. $>N-CH(Z)-CO-$ is a (D)-phenylalanine residue (whereby Z is benzyl).
11. B is —Phe— or —Tyr—.
12. C is —(D)Trp—.
13. D is —Lys— or —MeLys—, especially —Lys—.
14. E is the residue of a natural α-amino acid, especially —Thr—.
15. F is a group of formula $-CO-N(R_3)R_4$, especially a group of formula $-CO-N(R_3)-CH(R_5)-X$ (in which case $R_3=H$ or $CH_3$). In the latter case the moiety $-CH(R_5)-X$ preferably has the (L)-configuration.
15.1 $R_3$ is preferably hydrogen.
15.2 As the substituent attaching to the α-carbon atom of a natural amino acid (i.e. of formula $H_2N-CH(R_5)-COOH$, $R_5$ is preferably $-CH_2OH$, $-CH(OH)-CH_3$, isobutyl or benzyl, or $R_5$ is $-(CH_2)_2-OH$ or $-(CH_2)_3OH$. It is especially $-CH_2OH$ or $-CH(OH)-CH_3$.
15.3 X is preferably a group of formula $-CO-N(R_6)R_7$ or $-CH_2-OR_2$, especially of formula $-CH_2OR_2$ and $R_2$ is preferably hydrogen or has the meaning given under 16. below. Most preferably $R_2$ is hydrogen.
16. By the term "physiologically acceptable, physiologically hydrolysable ester" as applied to the definition of residues $R_2$ is meant esters with acids which are hydrolysable under physiological conditions to yield acids which are themselves physiologically tolerable at the applied dosage levels. As the residue of a physiologically acceptable, physiologically hydrolysable ester $R_2$ is preferably HCO, $C_{2-12}$-alkylcarbonyl, $C_{8-12}$phenylalkylcarbonyl or benzoyl.
17. Preferably the residues in the 2- and 7-positions have the (L)-configuration.
18. Preferably $Y_1$ and $Y_2$ together represent a direct bond.

A particularly interesting group of polypeptides of formula I are those wherein A represents an acyl residue incorporating an aliphatic moiety (e.g. as $R^I$, $R^{II}$, $R^{III}$ or $R^{IV}$ of the groups defined under 1. to 4. above) having at least 7 carbon atoms or $A_1$ is a group $R_9CONH-$ as defined under 6. above, wherein $R_9$ has at least 7 carbon atoms, compounds of this type (hereinafter referred to as "polypeptides of Type-T") being characterised by a more prolonged duration of activity when administered sub-cutaneously. Preferred "polypeptides of Type-T" are those wherein A is a group $R^ICO-$ wherein $R^I$ is $C_{7-15}$alkyl, preferably $C_{7-10}$alkyl. Especially preferred are "polypeptides of Type-T", wherein the remaining residues in formula I above have the significances specified under 6. through 18. above.

The polypeptides of the invention, e.g. of formula I, may exist in free, i.e. unprotected, or protected form, i.e. in which one or more reactive groups or atoms e.g. N-terminal amino groups, C-terminal carboxy groups or —SH groups are covered by a protecting group. Suitable protecting groups, e.g. N-, carboxy- and S-protecting groups are any of those known and commonly employed in the art of peptide chemistry, including such protecting groups as hereinafter employed in the accompanying examples. Generally protected forms will primarily be of use as intermediates e.g. for obtaining the unprotected peptides of the invention. However, where such protected forms are themselves pharmaceutically active, i.e. are useful as pharmaceuticals as hereinafter described, and physiologically tolerable at the desired dosage levels, e.g. as in the case where protecting groups present are cleavable under physiological conditions to yield the free peptides of the invention, e.g. compounds of formula I in free form and where the further cleavage product or products thereby obtained are themselves physiologically tolerable at the applied dosage levels, such protected forms will themselves be useful as pharmaceuticals, e.g. as pro-drugs. Such protected forms are defined hereinafter as "pharmaceutically applicable".

Polypeptides of the invention whether in free or protected form may also exist as salts or as complexes. Acid addition salts may be formed with e.g. organic acids, polymeric acids and inorganic acids. Such acid addition salt forms include e.g. the hydrochlorides and acetates. By complexes are to be understood compounds of known type, formed on addition of inorganic substances, e.g. inorganic salts or hydroxides such as Ca- and Zn-salts, and/or on addition of polymeric organic substances.

The polypeptides of the invention (whether in free or protected form) as well as their salts and complexes may be obtained by methods well known in the art of peptide chemistry, e.g. as described in the accompanying examples. Accordingly the present invention also provides, a process for the production of a polypeptide as hereinbefore defined, in particular a polypeptide of formula I above, in free or protected form, or a salt or complex thereof, which process comprises;

(a) removing at least one protecting group from a protected straight-chain or mono-cyclic polypeptide as hereinbefore defined (for example a protected polypeptide of formula I as hereinbefore defined) to obtain the corresponding poypeptide in free form;

(b) linking together by an amide bond two peptide units, each of which contains at least one amino acid or amino alcohol residue in free or protected form, the said peptides units being such that a straight-chain or mono-cyclic polypeptide as hereinbefore defined (for example a polypeptide of formula I as hereinbefore defined) is obtained in free or protected form, and, when required carrying out process step a);

(c) converting a functional group at the C-terminal of a straight-chain or mono-cyclic polypeptide as hereinbefore defined (for example the group F of a polypeptide of formula I as hereinbefore defined) in free or protected form, into another C-terminal functional group (for example another group F) and, when required, carrying out process step (a);

(d) oxidising a straight-chain polypeptide as hereinbefore defined (for example a polypeptide of formula I as hereinbefore defined, but wherein $Y_1$ and $Y_2$ are each hydrogen) in free or protected from, to obtain a mono-cyclic polypeptide as hereinbefore defined (for example a polypeptide of formula I as hereinbefore defined, but wherein $Y_1$ and $Y_2$ together are a direct bond) in free or protected form, and, when required, carrying out process step (a); and recovering the polypeptide in free or protected form thus obtained, either as such or as a salt or complex thereof.

In so far as the starting materials for the above process have not previously been described in the art, these may be produced and purified in accordance with techniques which are well-known in the art.

In the following examples $[\alpha]_D^{20}$ values are uncorrected. The following abbreviations are employed:

BOC=tert.-butoxycarbonyl
BTFA=boron-tris-trifluoroacetate
DMF=N,N-dimethylformamide
MBzl=p-methoxybenzyl
ONP=4-Nitrophenoxy
TFA=trifluoroacetic acid

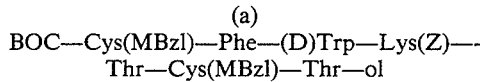

Thr—ol = the threoninol residue

Z=benzyloxycarbonyl

EXAMPLE 1

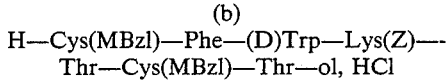

Benzyl-(D)Phe—Cys—Phe—(D)Trp—Lys—Thr—Cys—Thr—ol 0.95 g Benzyl—(D)Phe—Cys(MBzl)—Phe—(D)Trp—Lys(Z)—Thr—Cys(MBzl)—Thr—ol and 3.5 ml thioanisole are dissolved in 5 ml TFA at 0° C. The solution is cooled to −10° C., 15 ml ca.2 molar BTFA in TFA are added and the whole is stirred for 1,5 hrs. at −5° C. 50 ml cold (−60° C.) abs. methanol are added with stirring and the whole is stirred with a mixture of 12 ml ca. 5N HCl/ethyl ether in 3 liters of ethyl ether. The precipitated product is filtered off, washed with ethyl ether and dissolved immediately in a mixture of 3,5 liters dioxane/H₂O (7:3). The pH is adjusted to 7.5/8.0 by the addition of IN NH₄OH and the mixture stirred in an open vessel at room-temperature until it reacts negative to testing for —SH groups (e.g. Ellman test). The pH is adjusted to ca. 4.0 by addition of dilute HCl, the whole is concentrated under vacuum and lyophilised. The lyophilised product is purified chromatographically on silica gel with a chloroform/methanol/glacial acetic acid/H₂O mixture as eluant. Fractions containing the product compound are combined, concentrated under vacuum with the addition of H₂O and lyophilised to yield the title compound: $[\alpha]_D^{20} = -31°$ (c=0.50 in 95% acetic acid).

The starting material may be obtained as follows:

(a)
BOC—Cys(MBzl)—Phe—(D)Trp—Lys(Z)—Thr—Cys(MBzl)—Thr—ol 0.44 ml triethylamine and 1.6 g BOC—Cys(MBzl)—ONP are added to 3.6 g H—Phe—(D)Trp—Lys(Z)—Thr—Cys(MBzl)—Thr—ol, HCl (obtained analogously to examples 1a–1j of U.K. Patent specification No. 2,095,261 A (=New Zealand Patent Application No. 199911, filed Mar. 4, 1982), and the whole is stirred for 15 hours at room temperature.

The product is concentrated under vacuum, diluted with methanol and a little H₂O is added to effect precipitation. The precipitate is filtered off, washed with methanol and dried to yield the title compound: $[\alpha]_D^{20} = -15.5°$ (c=1.0 in DMF); M.P.=175° C.

(b)
H—Cys(MBzl)—Phe—(D)Trp—Lys(Z)—Thr—Cys(MBzl)—Thr—ol, HCl 3.5 g of the product of step (a) are dissolved in a mixture of 25 ml TFA/H₂O (9:1) at 0° C. and stirred for 45 min. also at 0° C. The obtained mixture is stirred in a mixture of 500 ml ethyl ether and 5 ml ca. 5N HCl in ethyl ether. The precipitated peptide is washed with ethyl ether and dried to yield the title compound: $[\alpha]_D^{20} = -16°$ (c=1.0 in 95% acetic acid); the product decomposes at 120° C.

(c) Benzyl—(D)Phe—NH—NH—BOC, HCl 0,36 ml benzaldehyde and 4 g 3 Å molecular sieve are added to 1 g H—(D)Phe—NH—NH—BOC dissolved in 50 ml methanol and the whole is stirred for ca. 15 hours at room temperature. A total of 650 mg NaCNBH₃ are then added portionwise under a nitrogen atmosphere over a period of 20 hours, the pH being maintained at each addition at ca. 6 by the addition of HCl in ethyl ether. The obtained product is filtered, the filtrate washed with methanol, concentrated under vacuum, diluted with ethyl ether, washed with H₂O and the ether-phase dried over Na₂SO₄ and added to 0.8 ml 5N HCl in ethyl ether. The precipitated product is filtered, washed with ethyl ether and dried to yield the title compound: $[\alpha]_D^{20} = -30.5°$ (c=1.0 in DMF); decomposing at 180° C.

(d) Benzyl—(D)Phe—NH—NH₂, HCl 0.50 g benzyl—(D)Phe—NH—NH—BOC, HCl are dissolved in 5 ml TFA, allowed to stand for 15 mins. at room temperature and then stirred into ca. 100 ml ethyl ether and 1 ml ca. 5N HCl/ethyl ether. The precipitated product is filtered off, washed with ethyl ether and dried to yield the title compound: $[\alpha]_D^{20} = -31°$ (c=1.0 in DMF); decomposing at 130° C.

(e)
Benzyl—(D)Phe—Cys(MBzl)—Phe—(D)Trp—Lys(-Z)—Thr—Cys(MBzl)—Thr—ol 0.35 g benzyl—(D)Phe—NH—NH₂, HCl in 20 ml DMF are cooled to −20° C. and 0.8 ml ca. 5N HCl in ethyl ether followed by 1.3 ml t. butylnitrite are added with stirring. The mixture is stirred for 10 mins. at −15° C., cooled to ca. −25° C. and 0.58 ml triethylamine followed by a cold (−10° C.) solution of 0.86 of the product of step (b) and 0.12 ml triethylamine in 10 ml DMF are added. The reaction mixture is stirred for 20 hours at −10° C. and then for ca. 16 hours at a temperature of from −5° to 0° C., the pH being maintained at 8.5–9.0 by the addition of triethylamine. The product mixture is concentrated under vacuum, diluted with methanol and the product precipitated by addition of H₂O. The precipitate is filtered off, washed with methanol/H₂O (1:1) and dried to yield the title compound: $[\alpha]_D^{20} = -17.3°$ (c=1.0 in DMF), MP=173° C.

The following compounds may be obtained analogously:

EXAMPLES 2-4 ploying at least 4 rats per dose. The rats are decapitated 60 minutes after administration, the blood is collected and the serum GH-level determined by radio-immunoassay.

Polypeptides in accordance with the invention are active in this test when administered at a dosage in the range of from 0,01 to 50 μg/kg s.c.

The above test may be adapted to determine effectiveness over prolonged periods of time, e.g. by decapitating 6 or 18 hours after administration. "Polypeptides of Type-T" as hereinbefore defined may be shown to be active in the above described test method when administered at dosages in the aforesaid range, over longer periods of time, e.g. up to 18 hours.

The said polypeptides (free or protected), salts and complexes are accordingly useful in the treatment of disorders with an aetiology comprising or associated with excess GH-secretion e.g. in the treatment of diabetes mellitus and angiopathy as well as of acromegaly.

The said polypeptides (free or protected), salts and complexes also inhibit gastric- and pancreatic secretion as indicated in standard animal tests, e.g. in accordance with the method described by Doepfner et al., Triangle 16, 2, 105 (1977) and by Konturek al., Scand. J. Gastroent. 6, 423 (1971).

Polypeptides in accordance with the invention are active in this test when administered at a dosage in the range of from 0,01 to 50 μg/kg.

The said polypeptides (free or protected), salts and

2.

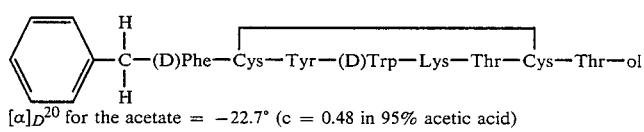

$[\alpha]_D^{20}$ for the acetate = −22.7° (c = 0.48 in 95% acetic acid)

3.

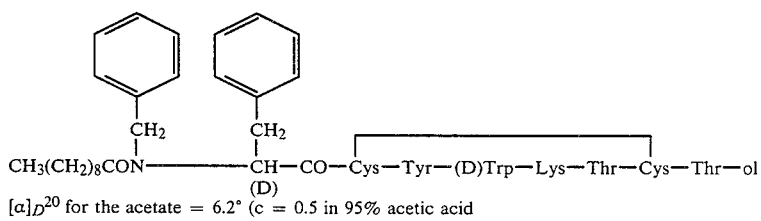

$[\alpha]_D^{20}$ for the acetate = 6.2° (c = 0.5 in 95% acetic acid

4.

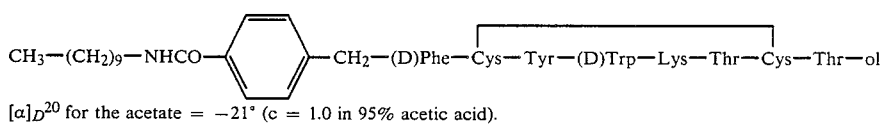

$[\alpha]_D^{20}$ for the acetate = −21° (c = 1.0 in 95% acetic acid).

EXAMPLES 5-8

Proceeding analogously to examples 1 to 4, but omitting the final oxidation step, the straight-chain polypeptides corresponding to each of the individual monocyclic polypeptides recited (i.e. wherein the —Cys— residues are not linked) are produced, as compounds 5 through 8.

Polypeptides of the invention, e.g. of formula I, in free or pharmaceutically applicable protected form as well as the pharmaceutically acceptable salts and complexes thereof, exhibit valuable pharmacological properties as indicated in animal tests. In particular they exhibit GH-secretion inhibiting activity as indicated e.g. by depression of serum GH-levels in the rat.

This test (TEST I) is carried out employing male rats under Nembutal narcosis. The test-substance is administered at varying, logarithmically staggered doses emcomplexes are thus useful in the treatment of gastrointestinal disorders for example in the treatment of gastric ulcer, gastro-intestinal bleeding and acute pancreatitis.

The pharmaceutically applicable protected forms of the polypeptides of the invention as well as the pharmaceutically acceptable salts and complexes of polypeptides of the invention show activity of the same order as the free compounds in the above described test methods.

For the above uses the dosage will, of course, vary depending on the compound employed, mode of administration and treatment desired. However, in general satisfactory results are obtained when administered at a daily dosage of from about 0,03 to about 150 μg/kg conveniently given in divided doses 2 to 4 times a day or in sustained release form. For larger mammals, the total daily dosage is in the range of from about 2 μg to about 10 mg polypeptide, and suitable unit dosage forms e.g. for parenteral administration contain from about 0,05 μg to about 5 mg, of polypeptide in accordance with the invention in free form or an equivalent amount of a pharmaceutically applicable protected form or of a pharmaceutically acceptable salt or complex thereof, together with a solid or liquid pharmaceutical diluent or carrier therefor.

The daily dosages suitable for any particular compound will, of course, depend on a number of factors including relative potency of activity. The preferred compound of the invention is the title compound of example 1. This compound has, for example, been determined to have an $ID_{50}$ in TEST I above of 0,02 μg/kg s.c. for activity at 60 minutes the determined $ID_{50}$ being the amount of compound required to effect 50% reduction fo the GH-level compared with untreated controls. For the known compound somatostatin, a determined $ID_{50}$ value in TEST I is 93 μg/kg s.c. for activity at 60 minutes. Thus an indicated daily dosage for the compound of example 1 for use as a GH-secretion inhibitor would be ca. 0,01 to 0,05% of the dosaging appropriate in the case of somatostatin.

In accordance with the foregoing the present invention further provides:

(1) a method of treating disorders with an aetiology comprising or associated with excess GH-secretion (such as diabetes mellitus, angiopathy and acromegaly) as well as of treating gastro-intestinal disorders (such as gastric ulcer, gastro-intestinal bleeding and acute pancreatitis), in a subject in need of such treatment, which method comprises administering to said subject an effective amount of polypeptide in accordance with the invention (in free or pharmaceutically applicable protected form) or a pharmaceutically acceptable salt or complex thereof; and (2) pharmaceutical compositions comprising a polypeptide in accordance with the invention (in free or pharmaceutically applicable protected form) or a pharmaceutically acceptable salt or complex thereof, together with a pharmaceutically acceptable diluent or carrier therefor.

We claim:

1. A polypeptide of formula I

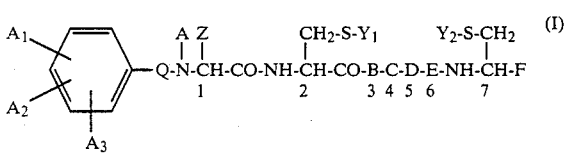

wherein

A is hydrogen, $C_{1-3}$alkyl or an acyl group of the formula
(a) $R^{I}CO$— wherein $R^{I}$ is $C_{1-20}$alkyl, $C_{3-20}$alkenyl, $C_{3-20}$alkinyl, phenyl, naphthyl or $C_{7-10}$(phenylalkyl);
(b) $R^{II}SO_2$— wherein $R^{II}$ is $C_{1-10}$alkyl, phenyl or $C_{7-10}$(phenylalkyl);
(c) $R^{III}O$—CO— wherein $R^{III}$ is $C_{1-10}$alkyl or $C_{7-10}$(phenylalkyl); and
(d)

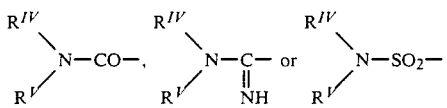

wherein
$R^{IV}$ is hydrogen, $C_{1-10}$alkyl, phenyl or $C_{7-10}$(phenylalkyl) and
$R^{V}$ is hydrogen or $C_{1-10}$alkyl;

$A_1$ is hydrogen, $C_{1-3}$alkyl, $C_{1-3}$alkoxy, halogen, OH, $NO_2$, esterified or amidated carboxy group of the formula

wherein
$R_8$ is $C_{1-16}$alkyl or an amide group of the formula $R_9$—CO—NH—
wherein
$R_9$ is $C_{1-15}$alkyl;

$A_2$ is hydrogen, $C_{1-3}$alkyl, $C_{1-3}$alkoxy, halogen, OH or $NO_2$,
$A_3$ is hydrogen, $C_{1-3}$alkyl or $C_{1-3}$alkoxy,
Q is $C_{1-4}$alkylene,
>N—CH(Z)—CO— is an (L)- or (D) phenylalanine residue optionally ring substituted by one or more members selected from the group consisting of halogen, $NO_2$, $NH_2$, OH, $C_{1-3}$alkyl and $C_{1-3}$alkoxy,
B is —Phe— optionally ring-substituted by one or more memebers selected from the group consisting of halogen, $NO_2$, $NH_2$, OH, $C_{1-3}$alkyl and $C_{1-3}$alkoxy,
C is —Trp— or (D)Trp— optionally α-N-methylated and optionally benzene-ring-substituted by one or more members selected from the group consisting of halogen, $NO_2$, $NH_2$, OH, $C_{1-3}$alkyl and $C_{1-3}$alkoxy,
D is —Lys— optionally α-N-methylated and optionally ε-N-$C_{1-3}$alkylated,
E is —Thr—
F is a group of formula —$COOR_1$, —$CH_2OR_2$,

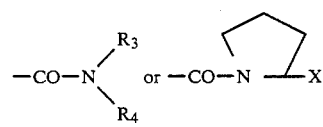

wherein
$R_1$ is hydrogen or $C_{1-3}$alkyl,
$R_2$ is hydrogen or the residue of a physiologically acceptable, physiologically hydrolysable ester,
$R_3$ is hydrogen or methyl,
$R_4$ is —$CH(R_5)$—X,
$R_5$ is hydrogen, —$(CH_2)_2$—OH, —$(CH_2)_3$—OH, —$CH_2OH$, —$CH(OH)$—$CH_3$ or isobutyl,
X is a group of formula —$COOR_1$, —$CH_2OR_2$ or —$CON(R_6)R_7$
wherein
$R_1$ and $R_2$ have the meanings given above,
$R_6$ is hydrogen or $C_{1-3}$alkyl and
$R_7$ is hydrogen, $C_{1-3}$alkyl, phenyl or $C_{7-10}$phenylalkyl,
the group —$CH(R_5)$—X having the (D)- or (L)-configuration, and $Y_1$ and $Y_2$ are each hydrogen or together represent a direct bond, whereby the residues in the 2- and 7-position each independently have the (L)- or (D)-configuration;
said polypeptide being in free or pharmaceutically acceptable protected form;
or a pharmaceutically acceptable salt or complex thereof.

2. A polypeptide according to claim 1 of the formula

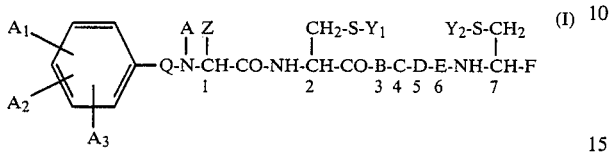

wherein

A is hydrogen, $C_{1-3}$alkyl or an acyl group of the formula
(a) $R^I CO$— wherein $R^I$ is $C_{1-20}$alkyl, $C_{3-20}$alkenyl, $C_{3-20}$alkinyl, phenyl, naphthyl or $C_{7-10}$(phenylalkyl);
(b) $R^{II}SO_2$— wherein $R^{II}$ is $C_{1-10}$alkyl, phenyl or $C_{7-10}$(phenylalkyl);
(c) $R^{III}O$—CO— wherein $R^{III}$ is $C_{1-10}$alkyl or $C_{7-10}$(phenylalkyl); and
(d)

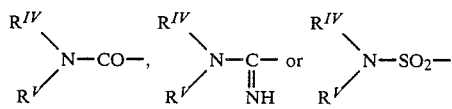

wherein $R^{IV}$ is hydrogen, $C_{1-10}$alkyl, phenyl or $C_{7-10}$(phenylalkyl) and $R^V$ is hydrogen or $C_{1-10}$alkyl;

$A_1$ is hydrogen, $C_{1-3}$alkyl, $C_{1-3}$alkoxy, halogen, OH, $NO_2$, an esterified or amidated carboxy group of the formula $R_8O$—CO— or $R_8$—NH—CO— wherein $R_8$ is $C_{1-16}$alkyl or an amide group of the formula $R_9$—CO—NH—
wherein
$R_9$ is $C_{1-15}$alkyl;

$A_2$ is hydrogen, $C_{1-3}$alkyl, $C_{1-3}$alkoxy, halogen, OH or $NO_2$, $A_3$ is hydrogen, $C_{1-3}$alkyl or $C_{1-3}$alkoxy, Q is $C_{1-4}$alkylene, $>$N—CH(Z)—CO— is an (L)- or (D)-phenylalanine residue optionally ring-substituted by halogen, $NO_2$, $NH_2$, OH, $C_{1-3}$alkyl and $C_{1-3}$alkoxy, B is —Phe— optionally ring-substituted by halogen, $NO_2$, $NH_2$, OH, $C_{1-3}$alkyl and $C_{1-3}$alkoxy, C is —Trp— or (D)Trp— optionally α-N-methylated and optionally benzene-ring-substituted by halogen, $NO_2$, $NH_2$, OH, $C_{1-3}$alkyl and $C_{1-3}$alkoxy, D is —Lys— optionally α-N-methylated and optionally ε-N-$C_{1-3}$alkylated, E is —Thr—

F is a group of formula —$COOR_1$, —$CH_2OR_2$,

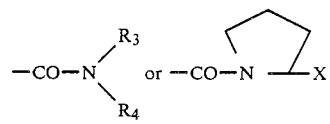

wherein $R_1$ is hydrogen or $C_{1-3}$alkyl, $R_2$ is hydrogen or the residue of a physiologically acceptable, physiologically hydrolysable ester, $R_3$ is hydrogen or methyl, $R_4$ is —CH($R_5$)—X, $R_5$ is hydrogen, —$(CH_2)_2$—OH, —$(CH_2)_3$—OH, —$CH_2OH$, —CH(OH)—$CH_3$ or isobutyl, X is a group of formula —$COOR_1$, —$CH_2OR_2$ or —$CON(R_6)R_7$
wherein
$R_1$ and $R_2$ have the meanings given above,
$R_6$ is hydrogen or $C_{1-3}$alkyl and
$R_7$ is hydrogen, $C_{1-3}$alkyl, phenyl or $C_{7-10}$phenylalkyl,
the group —CH($R_5$)—X having the (D)- or (L)-configuration, and $Y_1$ and $Y_2$ are each hydrogen or together represent a direct bond, whereby the residues in the 2- and 7-position each independently have the (L)- or (D)-configuration, or a pharmaceutically acceptable salt or complex thereof.

3. A polypeptide according to claim 1 of the formula

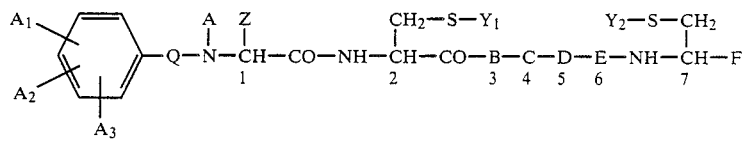

wherein

A is hydrogen, $C_{1-3}$alkyl or $R^I CO$— or $R^{II}SO_2$— wherein $R^I$ is $C_{1-15}$alkyl or $C_{7-10}$(phenylalkyl) and $R^{II}$ is $C_{1-10}$alkyl or phenyl $A_1$ is hydrogen, $R_8O$—CO—, $R_8$—NH—CO— or $R_9$—CO—NH— wherein $R_8$ is $C_{1-16}$alkyl and $R_9$ is $C_{1-15}$alkyl, $A_2$ is hydrogen, $A_3$ is hydrogen, Q is methylene, $>$N—CH(Z)—CO is a (D)-phenylalanine residue, B is —Phe— or —Tyr—, C is —(D)—Trp—, D is —Lys— or —MeLys—, E is —Thr—, F is —CO—N($R_3$)—CH($R_5$)—X,
wherein
$R_3$ is hydrogen or methyl,
$R_5$ is —$(CH_2)_2$—OH —$(CH_2)_3$—OH, —$CH_2OH$, —CH(OH)—$CH_3$ or isobutyl
X is —$CH_2OR_2$ or —$CON(R_6)R_7$
wherein R₂ is hydrogen or the residue of a physiologically acceptable, physiologically hydrolysable ester, R₆ is hydrogen or C₁₋₃alkyl and R₇ is hydrogen, C₁₋₃alkyl, phenyl or C₇₋₁₀phenylalkyl, the group —CH(R₅)—X having the (D)- or (L)-configuration, and Y₁ and Y₂ are each hydrogen or together represent a direct bond, whereby the residues in the 2- and 7-position each independently have the (L)- or (D)-configuration, or a pharmaceutically acceptable salt or complex thereof.

4. A polypeptide according to claim 1 of the formula

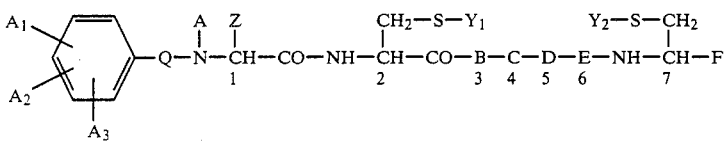

wherein

A is hydrogen, C₁₋₃alkyl or R^I CO— wherein R^I is C₁₋₁₀alkyl,

A₁ is hydrogen,

A₂ is hydrogen,

A₃ is hydrogen,

Q is methylene,

>N—CH(Z)—CO— is a (D)-phenylalanine residue,

B is —Phe— or —Tyr—,

C is —(D)Trp—,

D is —Lys—,

E is —Thr—,

F is —CO—NH—CH(R₅)—X,

R₅ is —CH₂OH— or —CH(OH)—CH₃,

X is —CH₂OH, and

Y₁ and Y₂ together are a direct bond, the group —CH(R₅)—X having the (D)- or (L)-configuration and the cysteine residue in the 2- and 7-position having the (L)-configuration, or a pharmaceutically acceptable salt or complex thereof.

5. The polypeptide according to claim 1 which is benzyl—(D) Phe—Cys—Phe—(D)Trp—Lys—Thr—Cys—Thr—ol.

6. The polypeptide according to claim 1 which is

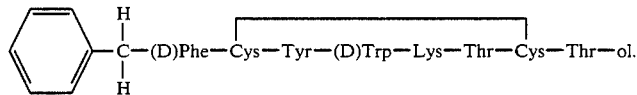

7. The polypeptide according to claim 1 which is

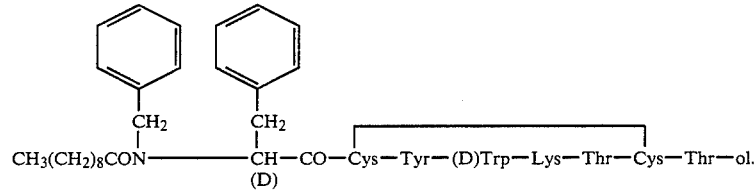

8. The polypeptide according to claim 1 which is

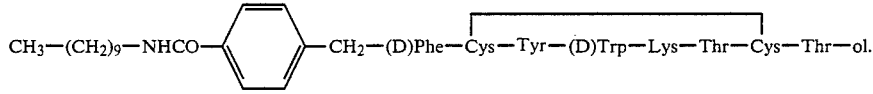

9. The polypeptide according to claim 1 which is

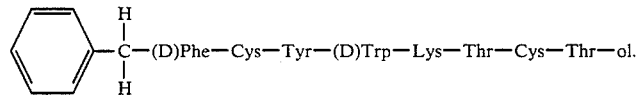

10. The polypeptide according to claim 1 which is

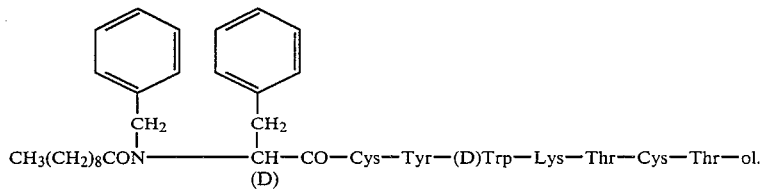

11. The polypeptide according to claim 1 which is

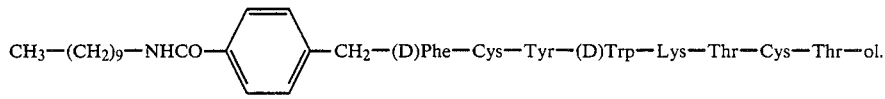

12. A polypeptide according to claim 1 of formula

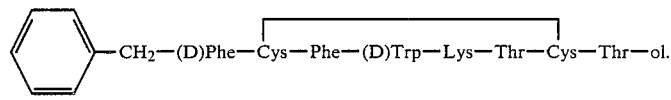

in free or pharmaceutically applicable protected form; or a pharmaceutically acceptable salt or complex thereof.

13. A method of treating disorders with an aetiology comprising or associated with excess GH-secretion, in a subject in need of such treatment, which method comprises administering to said subject an effective amount of polypeptide as defined in claim 1 (in free or pharmaceutically applicable protected form) or a pharmaceutically acceptable salt or complex thereof.

14. A method according to claim 13 for the treatment of diabetes mellitus, angiopathy or acromegaly.

15. A method of treating gastro-intestinal disorders in a subject in need of such treatment, which method comprises administering to said subject an effective amount of polypeptide as defined in claim 1 (in free or pharmaceutically applicable protected form) or a pharmaceutically acceptable salt or complex thereof.

16. A method according to claim 15 for the treatment of gastric ulcer, gastro-intestinal bleeding or acute pancreatitis.

17. A pharmaceutical composition comprising a polypeptide as defined in claim 1 (in free or pharmaceutically applicable protected form) or a pharmaceutically acceptable salt of complex thereof, together with a pharmaceutically acceptable diluent or carrier therefor.

* * * * *